United States Patent [19]

Kummer

[11] Patent Number: 4,973,332
[45] Date of Patent: Nov. 27, 1990

[54] ATTACHMENT FOR FEMUR SLIDING SCREW PLATE

[75] Inventor: Frederick J. Kummer, Brooklyn, N.Y.

[73] Assignee: Hospital for Joint Diseases, New York, N.Y.

[21] Appl. No.: 242,650

[22] Filed: Sep. 12, 1988

[51] Int. Cl.⁵ .................................................. A61F 5/00
[52] U.S. Cl. ........................................ 606/65; 606/67; 606/73
[58] Field of Search ....... 128/92 YV, 92 ZW, 92 YS, 128/92 YP, 92 YF, 92 Z, 92 YZ, 92 YE, 92 YK, 83, 92 R; 411/461, 463, 462, 544, 545, 531; 606/65–68, 72–73, 59, 53, 104

[56] References Cited

U.S. PATENT DOCUMENTS

| | | | |
|---|---|---|---|
| 2,397,545 | 4/1946 | Hardinge | 128/92 YV |
| 2,414,882 | 1/1947 | Longfellow | 128/83 |
| 2,441,765 | 5/1948 | Hopkins | 128/92 YK |
| 2,489,870 | 11/1949 | Dzus | 128/92 YF |
| 2,702,543 | 2/1955 | Pugh | 128/92 YV |
| 2,801,631 | 8/1957 | Charnley | 128/92 YV |
| 3,002,514 | 10/1961 | Deyerle | 128/92 YK |
| 3,025,853 | 3/1962 | Mason | 128/92 YK |
| 3,489,143 | 1/1970 | Halloran | 128/92 YK |
| 3,842,825 | 10/1974 | Wagner | 128/92 YV |
| 3,939,498 | 2/1976 | Lee | 128/92 YP |
| 4,003,376 | 1/1977 | McKay | 128/69 |
| 4,101,985 | 7/1978 | Baumann | 128/92 YV |
| 4,120,298 | 10/1978 | Fixel | 128/92 YK |
| 4,172,452 | 10/1979 | Forte | 128/92 YZ |
| 4,438,762 | 3/1984 | Kyle | 128/92 YV |
| 4,488,543 | 12/1984 | Tornier | 128/92 R |
| 4,506,662 | 3/1985 | Anapliotis | 128/92 YF |
| 4,565,193 | 1/1986 | Streli | 128/92 YK |
| 4,573,458 | 3/1986 | Lower | 128/92 Y |
| 4,628,923 | 12/1986 | Medoff | 128/92 YV |
| 4,651,724 | 3/1987 | Berentey | 128/92 YP |
| 4,773,402 | 9/1988 | Asher | 128/92 YP |

FOREIGN PATENT DOCUMENTS 2090745  7/1982  United Kingdom .......... 128/92 YV

*Primary Examiner*—Robert A. Hafer
*Assistant Examiner*—Michael Brown
*Attorney, Agent, or Firm*—Stephen E. Feldman

[57] ABSTRACT

A femur sliding screw plate is improved by adding flanges or wings on either side of a central portion, the flanges extending at least partially around the femur shaft. Preferably, the flanges are provided integral to a centrally raised part which fits over a portion of the leg of a basic screw plate. Screw holes in the sliding screw plate align with screw holes in the basic screw plate and the sliding screw plate is attached to the basic screw plate and each screw plate is attached to the femur by common screws. The flanges each have screw holes, offset from the screw holes in the centralloy raised portion, screws being used to secure the flanges to outlying portions of the femur shaft in order to more fully consolidate fragments of the fractured femur. Alternatively a screw plate is provided with integral flanges extending from the leg of the screw plate.

8 Claims, 2 Drawing Sheets

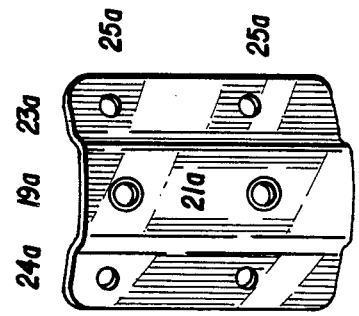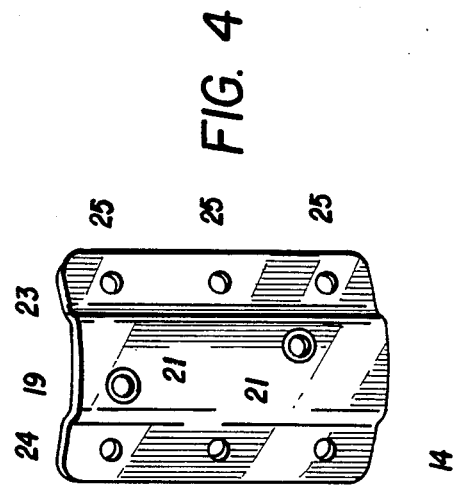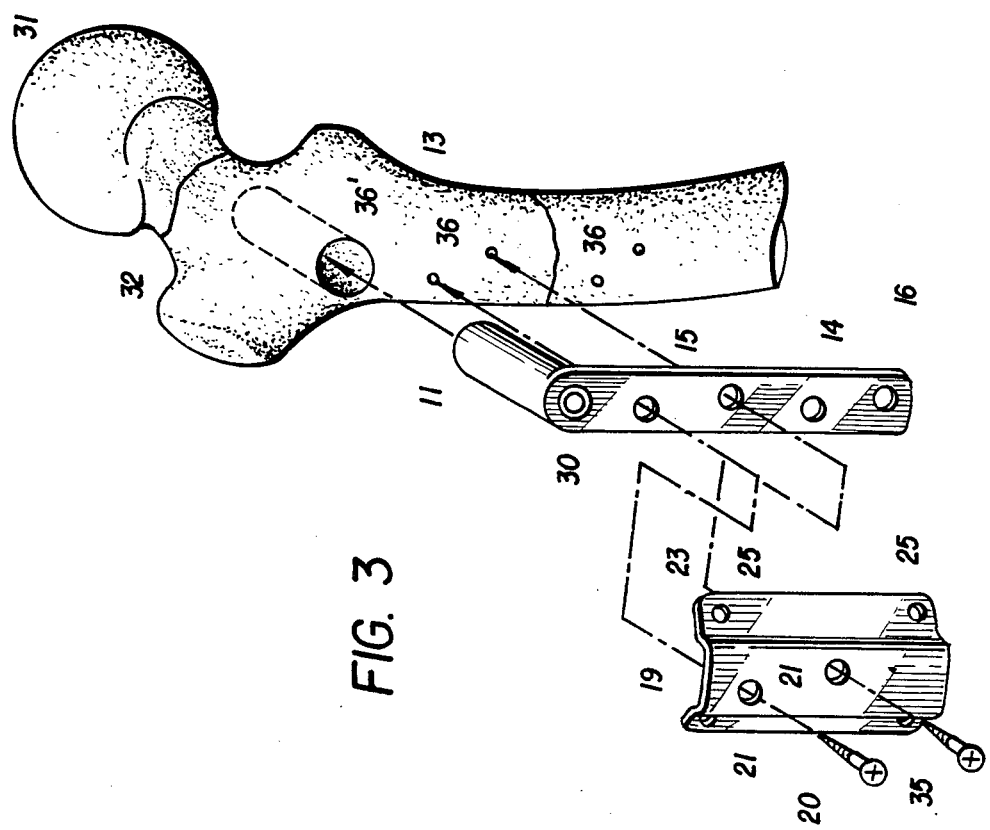

ATTACHMENT FOR FEMUR SLIDING SCREW PLATE

BACKGROUND OF THE INVENTION

1. Field of the Invention

This invention relates to bone plates for internal fixation of fractures of the femur bone. In particular the present invention relates to sliding screw or impaction nail plates particularly useful for repair of a fractured femur. The invention is particularly useful for providing more secure support and consolidation of femur bone fragments from intertrochanteric and subtrochanteric fractures.

2. Prior Art

A wide variety of implantable bone plates are known in the art for support and fixation of bone fracture. Since the breakage or fracture of bones in the body is not limited to size of person or bone implantable plates of different sizes and shape need be made readily available. This calls for the carrying of a large inventory of plates and screws for the various bones expected to be fractured and in need of fixation.

There are approximately 150,000 to 200,000 hip fractures each year in the United States alone. Approximately half of these hip fractures are intertrochanteric and/or subtrochanteric fractures. Quite often the plate implants that are available for repair of such fractures, such as sliding hip screw plates or impaction nail plates do not provide for sufficient attachment to secure all the bone fragments.

There has been, therefore, a need for a means or method for improving currently used implantable plates. The present invention addresses that need.

U.S. Pat. No. 4,488,543 appears to address the problem of preventing screw back out, that is, preventing the screws holding screw plates to the bone, from backing out of the bone. The structure taught in this patent addresses the security of screws attaching the plate to the bone but fails to provide for extended coverage of bone area as needed and fails to provide for holding bone fragments where required.

Other patents teach structure of implant plates, such as pronged plates for resetting fractured bones, as in U.S. Pat. No. 4,565,193 and the pronged bone joining plate taught in U.S. Pat. No. 4,651,724 and the elongated rod bone plate of U.S. Pat. No. 4,573,458, but none of these patents address the problems of providing more direct stability and security for the bone fragments of the fractured bone.

THE PRESENT INVENTION

The present invention is an improved femur implant screw plate system or improved femur implant plate which provides more stability and security for bone fragments of the fractured femur effectively consolidating the bone fragments more efficiently and securely than accomplished by existing plates without the adverse effect on the femur of using too many flanges that extend beyond the sides of the basic screw plate providing additional screw attachment points to the femur shaft and more bone fragment consolidation than heretofore provided. The body of the supplemental plate, which fits over the leg of the implant screw plate, has screw holes that align with screw holes in the leg of the basic screw plate. This makes possible combining the attachment plate to the leg of the basic screw plate and the attaching of the attachment plate and the leg of the basic screw plate to the femur shaft all with the same screws. This supplemental plate may be used selectively, as the condition of the fractured femur may require This supplemental attachment plate is particularly useful for reinforcement for subtrochanteric fractures where it may be necessary to pull multiple bone fragments together and hold the bone and fragments securly.

From one aspect, the present invention is a winged attaching or reinforcing plate which compliments, aguments, reinforces and/or backs-up a femur screw plate of the type that at least has an elongated leg or section that essentially parallels the femur when used and is attached to the femur by screws. The winged attaching plate forms a partial overlay of a femur screw plate providing a back-up which fits over the screw plate extending beyond the sides of the plate so as to extend around the femur shaft for providing additional security by according additional attachment to the femur and providing consolidation of the fragmented femur. The wings of the reinforcing plate, which extend beyond the femur screwplate, have holes permitting attachment of the reinforcing plate to the femur shaft at points beyond the normal attachment points of the basic screw plate. The reinforcing plate also has centrally disposed screw holes that mate or align with the screw holes of the basic femur screw plate which permits combining the system parts and the system to the bone without adverse increase in the number of screws used in attaching the system to the femur shaft.

By providing a reinforcing augmentation that complements and fits over existing types of sliding screw plates rather than providing screw plates with flanges as an integral part of the screw plate, the inventory of screw plates and retaining screws that must be maintained in a large degree of sizes can be kept to a minimum. Not every femur fracture requires the additional stabilization provided by the winged attachment plate of this invention. An advantage of the present invention is that the invention may be used selectively.

In those cases of femur fracture that do require more security and/or consolidation than that accorded by an unreinforced femur sliding screw plate, the normal femur screw plate may be readily augmented and/or reinforced by complementing the normal femur screw plate with the present invention. This selection of overlay capability of a bilateral screw plate system accords the surgeon a greater degree of flexibility relating to the implant used on the fractured bone, and is the preferred structure of the invention.

It is, however, within the scope of this invention to provide flanges or wing sections to femur screw plates for more fully encompassing the femur, as an integral part of the implant screw plate. This embodiment is less desirable, however, because although the winged structure provides a greater coverage and more attachment points than currently used femur screw plates, the back-up and selection factors of a multicomponent screw plate system are absent. In addition, the use of a winged configuration screw implant plate would require greatly increased inventory since different sizes of implant plates of both normal configuration and winged configuration would become part of the inventory.

From another aspect, the present invention is a greatly improved and more versatile femur implant screw plate system which comprises an elongated sliding screw plate that is designed to be attached to the femur in an essentially parallel relationship, lying along the femur shaft. The elongated plate has at least two longitudinally disposed holes for accepting attaching screws which pass through the holes and are screwed into the femur shaft with the shoulder of the screws impinging on the screw plate for attaching the screw plate to the femur, the sliding screw plate system having on either side flanges, each of which extend at least 0.3 inches beyond the edge of the spine of the basic screw plate, and are curved to fit at least approximately the curvature of the femur shaft and has at least two additional screw holes permitting screw attachment of the flanges to the femur shaft. The flanges accord a greater affixation of the sliding screw plate system to the femur bone and more secure and greater embracement of femur bone for greater consolidation and support of the fractured and/or fragmented bone. Preferably the flanges or wing sections of the improved femur sliding screw plate system are provided by a flange bearing or winged attachment plate which is positioned, relative to the basic screw plate so that the attachment plate is in overlayed position or spans at least a part of the basic screw plate, augmenting the basic screw plate and supplementary thereto. The attachment is provided with screw holes which mate or align with centrally disposed screw holes in the basic screw plate of the system.

The preferred embodiment of the invention, as described below is an attachment plate for a femur sliding screw plate. The sliding screw plate is used by attaching the screw plate to the surface of the femur bone by screws passing through screw holes in the leg of the plate and screwed into the bone holding the plate to the bone. The screw plate lies essentially along the femur shaft in parallel relationship with the femur bone having the main purpose to hold together and reinforce the fractured femur bone. Preformed screw holes in the screw plate permit attaching screws to be screwed into the femur bone at the femoral neck, shaft and head. The attaching screws and the position of their insertion into the bone are designed to provide reinforcement to the fractured femur bone. The screw plate has at least two screw holes particularly designed and positioned to strengthen and provide additional assistance to or support to the fractured bone. These centrally-located screw holes provide passage through the screw plate for femur shaft screws which are screwed into the femur shaft. The alignment of the centrally-disposed screw holes in the attachment plate with the centrally-disposed screw holes in the leg of the basic screw plate permits attachment of the auxilliary screw plate to the based screw plate.

The attachment plate comprises a support plate designed to augment, reinforce and supplement a femur sliding screw plate, the attachment plate being of a generally rectangular configuration, having a centrally located, longitudinal humped configuration so as to fit snuggly over a part of the screw plate, and having at least two spaced access holes or screw apertures which match or align with at least two screw holes in the body of the screw plate allowing passage of screws there through for screwing femur shaft screws into the femur shaft and having, on either side, flanges or wing sections, each of which extends at least 0.3 inches beyond the edge of the screw plate and each is curved to fit, at least approximately, the curve or roundness of the femur shaft. Each flange has at least two screw holes permitting attachment of the respective flange to the femur shaft by screws.

BRIEF DESCRIPTION OF THE DRAWINGS

FIG. 3 is an exploded view of FIG. 2;

FIGS. 4 and 4a are two different structural designs of the sliding screw plate with alternate centrally positioned screw holes.

DETAILED DESCRIPTION OF THE INVENTION

Figure 1:
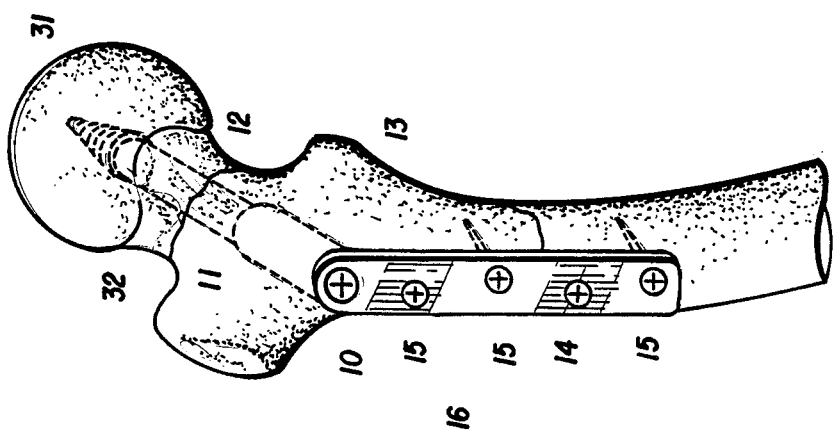
FIG. 1 is an illustration of a known implant screw plate attached by screws to a right femur.

With reference to FIG. 1 there is illustrated what is known as a RICHARDS BARROL PLATE attached to a right femur. This plate is used as an implant affixed to the outer surface of a femur for holding the fractured parts of a femur together to promote healing of the fractured bone. Although a RICHARDS BARROL PLATE is illustrated, this implantable plate is intended to represent any screw plate or impaction nail plate that may be used to hold together and support a fractured femur, such as illustrated. For the sake of clarity these implantable components will be referred to as "screw plate".

The screw plate generally consists of an end flange 10 which supports a barrol or neck 11. The barrol 11 is inserted into a pre-drilled hole 36' (seen in FIG. 3) and held therein by a lag screw 12. The lag screw extends into the ball of the femur holding that portion of the fractured femur together. A fracture is indicated as extending across the neck 32 of the femur. The screw plate 16 extends downward (in the illustration) into a leg 14 which lies along the exterior surface of the femur shaft and is affixed to the femur shaft by retaining screws 15, which are screwed into the femur shaft.

Figure 2:
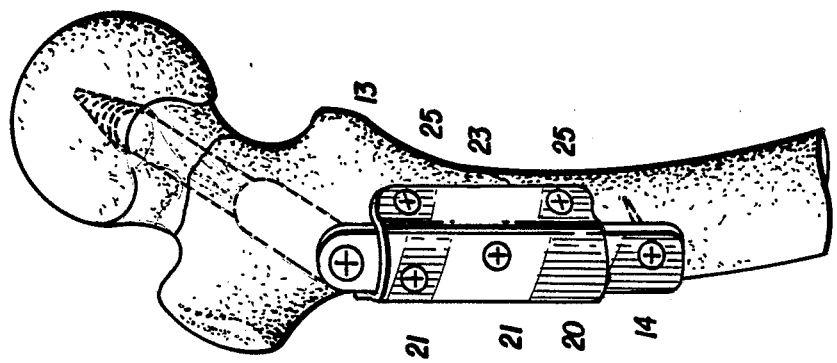
FIG. 2 is a illustration of a femur implant screw plate system showing an attachment plate secured in place over a femur implant screw plate, the system being screw secured to a femur.

The sliding screw plate of the present invention may be positioned over the leg 14 of the basic screw plate of FIG. 1, as shown in FIGS. 2 and 3. The present attachment plate is referred to as a sliding screw plate because the screw plate of the present invention may be slid up or down the leg 14 and the screw holes in the sliding screw plate may be aligned with screw holes in the leg of the screw plate and the two plates may be combined together and both affixed to the femur shaft using common screws.

Referring to FIGS. 2 and 3, an attachment or sliding screw plate form of the present invention comprises a unitary plate 20 having a rise or spine or hump 19 extending across the middle of a generally rectangular structured plate. The rise 19 extending longitudinally is a function of the localization of the attachment plate. The raised portion or hump 19 is structured to fit over a portion of the leg 14 of the screw plate. A pair of holes 21, located in the raised portion 19 of the attachment plate are spaced so as to align with a pair of holes in the leg 14 of the screw plate. The screw holes 21 are preferably counter sunk so that heads of screws when seated therein will be flush with the outer surface of the attachment plate and yet secure the attachment plate 20 to the leg 14 of the basic screw plate.

When the attachment plate, as shown in FIG. 2 is layed over the screw plate of FIG. 1 and screw holes of both plates are in alignment the threaded shafts of screws may be passed through the aligned holes and the screws screwed into the femur shaft so as to affix both the screw plate and the attachment plate to the femur shaft and to affix the attachment plate to the screw plate, combining the plates into a system. (see FIG. 3.)

In FIGS. 2 and 3, attachment of the sliding screw plate to the leg of the basic screw plate is made by using the two upper screw holes of the basic screw plate. However, if the location of the fracture requires, the attachment plate may be slid down the basic screw plate and attached by using lower screw holes on the leg.

In an alternate structure the holes 21 may be made sufficiently large to pass the femur screws through the attachment plate. However, this alternate structure relies on the screws in the flanges of the attachment plate to affix the attachment plate to the plate and to affix the attachment plate to the femur shaft. In both the preferred embodiment and in the alternate embodiment the spine portion 19 of the attachment plate fits over a portion of the leg 14 of the basic screw plate, effectively contouring the screw plate.

The attachment plate 20 of FIG. 2 has flanges or wing portions 23 extending from both sides of the central raised portion 19. An extension of at least three-tenths of an inch (0.3 inches) is preferred, from the longitudinal edges of the spine or raised portion 19. The flanges 23 may be made curved to provide an approximate fit to the femur shaft and/or may be malleable enough to permit bending to conform to the curvature or contour of the femur shaft along which the flanges will lie when attached to the screw plate.

Each of the flanges 23 and 24 include therein holes or apertures 25 for permitting the passage of screw shafts there through so that screws may be screwed into the femur shaft and affix the attachment plate to the femur shaft at points remote from the fixation points of the basic screw plate. This augmentation to the screw plate makes the screw plate more complete, extends the coverage of the screw plate to that of the fermur screw plate system, strenghtens the screw plate when added strength is apparently needed, when the nature of the fracture of the femur is considered and consolidates or holds together the fragmented pieces of the fractured bone.

The attachment screws are preferably cannulated. This permits pilot holes to be drilled into the bone and a probe or wire inserted into the pre-drilled holes and x-rayed to assure that the targeted bone fragment has been properly penetrated. Thereafter, the cannulated screw can be passed through the holes in the screw plates and into the pre-drilled holes and screwed into the bone in a known manner and secured. Preferably, screws having a diameter of at least 5.5 mm are used to pass through the holes 21 and through the holes in the leg 14 for attaching the attachment plate and the screw plate to the femur. The length of the screws depend on the diameter of the femur shaft. The screws for holes 25 are preferably somewhat smaller in diameter, for example 4 mm and sufficiently short in length to avoid passing through the femur shaft.

It will be appreciated that the screw holes 25 are preferable offset horizontally from the screw holes 21, as shown. This prevents interference between screws inserted in the holes 25 and those inserted in the holes 21.

Turning particularly to FIG. 3, an improved femur screw plate system is illustrated in exploded view as attached to a right femur. The upper portion 30 supports a barrol 11 inserted into a hole drilled into the femur bone 13. The lag screw 12 (see FIG. 1) extending through a hole 36' in neck 11 supports the femur head 31 with respect to the femur neck 32. The screw plate leg 14, extending from the upper portion 30, is attached to the femur shaft 13, such as also illustrated in FIG. 1. However, in the illustration in FIG. 3, pilot holes 36 are drilled into the femur shaft 13 and the screws 35 are made to pass through the holes 21 and 15 so that when the screws are screwed into the shaft of the femur and the heads of the screws are set in the countersunk shoulders of the spine 19 the sliding screw plate will be attached to the leg of the basic screw plate and both the sliding screw plate and the basic screw plate will be attached to the shaft of the femur by the same screws. This screw attachment combines the two screw plates into the femur screw plate system. The hole 36' in the upper part of the femur is a hole drilled into the bone, following acceptable medical procedure, so that the barrol of the screw plate may be inserted into the bone. During the initial stages of the operation the curvature of the flanges 23 and 24 are adjusted with respect to the contour of the shaft 13. Screws are inserted through the holes 25 and screwed into the femur shaft. The screws are seated against the countersunk shoulders of the holes 25 of the flanges 23 and 24 and thus fully secure the screw plate system to the femur and secure the bone fragments in position to promote healing.

Referring to FIGS. 4 and 4a two structures of the sliding attachment screw plate are illustrated, without limitation. In FIG. 4 the attachment plate 14 is illustrated in generally rectangular form with the center longitudinal section or spine 19 raised so as to fit over the leg of the basic screw plate. The holes 21 are centrally positioned so as to align with screw holes in the basic screw plate. Screw holes in the attachment plate are countersunk so that the tapered shoulders of retaining screws may secure the attachment plate to the leg of the basic screw plate and both plates to the femur bone when screws are seated in the countersunk holes.

Each flange 23 and 24 is fitted with three (3) screw holes, each of the flange screw holes being offset from the horizonal position of the screw holes in the spine of the attachment. These screw holes are also countersunk.

FIG. 4a illustrates another structure of sliding attachment plate where the flanges or wings 23a and are offset somewhat from the spine 19a. The screw holes 21a are illustrated in spaced, vertical alignment along the spine 19a. Each flange 23a and 24a is shown with two (2) screw holes. The flange screw holes are offset horizonally and vertically from the screw holes 21a, in the spine or raised portion 19a.

It should be kept in mind that the material out of which the flanged screw plate is made is not critical so long as the material is strong enough to carry out the function for which the component was made and the material of the component will not be rejected by the body after implantation. Stainless steel is preferred, although other metals may also be used. Some forms of plastic are also acceptable, so long as there is no body rejection and the material withstands the strains of back-up and functions properly to hold and support the bone fragments of the fractured femur, all to the ultimate objective, to promote healing of a fractured femur.

It will be noticed that throughout the drawings, where practical, identical and/or similar parts have been numbered with identical or similar call-out numbers.

Figure 5:
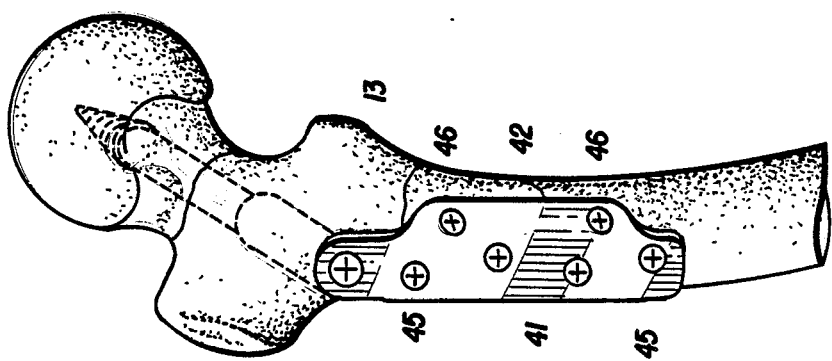
FIG. 5 is an illustration of an alternate embodiment of the invention.

FIG. 5 illustrates an alternate structure of the invention where flange 42 on the leg 41 of a screw plate are shown with the screw plate attached to a right femur. Although only one flange 42 is illustrated it is apparent that a second flange extends from the leg 41 at its other side (not shown).

The flanges on the screw plate in FIG. 5 are integral with the screw plate leg. The shape of the flanges may be as shown in FIG. 5 or may vary somewhat in shape, such as represented in FIGS. 4 and 4a. The length of the leg is a factor in determining how many screw holes, and therefore how many retaining screws, are used for each screw plate.

As to the flanges, FIGS. 2, 3, 4a and 5 illustrate two screw holes, and therefore two retaining screws per flange. FIG. 4, however, shows three (3) screw holes for each flange. The number of screws used for securing a flange to the surface of the femur shaft depends upon the length of the flange. However, care should be taken to avoid the use of too many screws or closely-spaced screws since too many screws and/or closely-spaced screws may unduly weaken the femur shaft, with adverse effect.

Although the present invention is preferably used in association with plates attached to the femur shaft by screws, it will be apparent that impaction nail plates can be used as the basic bone support plate and nails may be used, instead of screws, to secure the components to each other and each of the components to the femur shaft.

Thus there has been described and illustrated a preferred embodiment of the invention along with an alternate embodiment. Structures instrumental to securing or retaining the component of the invention to the bone have been illustrated and commented upon, with alternate structures suggested, without limitations. Other changes and/or modifications may be made, as will become apparent to those skilled in the art, without departing from the invention as defined in the claims.

What I claim is:

1. An attachment for a femur screw plate, said femur screw plate in use being secured through a femoral neck to a femoral head said screw plate having a screw plate leg that lies along the femur shaft and ends at its upper end in a flange through which at least a screw is passed into said femoral head, said screw plate leg having at least first and second screw holes for passage of femur shaft screws therethrough and into a femur shaft, said attachment comprising a support plate:
   (a) of a generally rectangular configuration;
   (b) having a longitudinal humped configuration for fitting snugly over said screw plate leg;
   (c) having at least first and second spaced screw apertures aligning with said at least first and second screw holes respectively for allowing passage of said femur shaft screws through both said support plate and said screw plate leg for securing said femur shaft screws in said femur shaft, for securing said support plate against said screw plate leg and said screw plate leg against said femur shaft and
   (d) said support plate having on either side thereof one flange each, each of which:
      (i) extends at least 0.3 inches beyond the edge of said screw plate leg;
      (ii) is curved to fit at least approximately, the curve of the femur shaft,
      (iii) has at least two lateral screw holes per flange, each screw hole permitting attachment of the flange to the femur shaft by screws passing therethrough,
   said attachment permitting a more secure approximation of femur bone fragements.

2. A reinforcing plate for combining with a leg of a femur screw plate, which in use lies along a femur shaft and wherein said leg has at least two holes therein for permitting passage of femur shaft securing means therethrough for entering into the femur shaft, said reinforcing plate having a longitudinal femur configurations for fitting over said leg of said femur screw plate and having lateral extensions which extend laterally beyond said leg and partially around said femur shaft, each extension of said reinforcing plate having holes therein for permitting attachment of said reinforcing plate to said femur shaft by securing means passing therethrough.

3. A reinforcing plate as in claim 2 and in which said femur shaft securing means are screws.

4. A reinforcing plate for combining with a femur screw plate, wherein said femur screw plate has a screw plate leg and in use said screw plate leg lies along a femur shaft, said screw plate leg including at least two screw holes for passage of shafts of femur shaft screws through said screw plate leg and into said femur shaft for securing said femur screw plate to the exterior of said femur shaft, said reinforcing plate comprising:
   (a) a raised member extending along the length of said reinforcing plate, said raised member adapted to fit over a portion of said screw plate leg; and
   (b) said reinforcing plate having flanged edges which extend out from and beyond both edges of said raised member and each flanged edge concavely curved for fitting partially around said femur shaft, each said flanged edge of said reinforcing plate having screw holes for permitting passage of shafts of femur shaft screws through the respective said flanged edge for securing said reinforcing plate to said femur shaft.

5. A femur shaft screw plate for attachment to a femur shaft for holding together fragmented pieces of a fractured femur bone, said femur shaft screw plate comprising:
   (a) a screw plate leg having a first length which when said femur shaft screw plate is positioned on said femur shaft extends along the length of said femur shaft, said first length defined by a first end of said screw plate leg and a second end of said screw plate leg;
   (b) a first flange and a second flange, each connected to opposite sides of said screw plate leg and each extending along part of said first length and each extending beyond the respective side to which the respective flange is connected, said first flange and said second flange each extending beyond said first end of said screw plate leg and each terminating short of said second end of said screw plate leg;
   (c) said screw plate leg having a screw holes disposed along said first length for receiving femur shaft attaching screws for attaching said femur shaft screw plate to said femur shaft; and
   (d) said first flange and said second flange each curved in concave configuration and having screw holes disposed in each respective flange for receiving femur shaft attaching screws for securing each respective flange to said femur shaft at opposite sides of said screw plate leg for supporting bone fragments of a fractured femur.

6. The femur shaft screw plate of claim 5 wherein said first flange and said second flanges are part of an attachment plate superposed over said screw plate leg, said attachment plate having at least two centrally-disposed screw holes aligning with said screw holes of said screw plate leg through which screws can be passed into said femur shaft securing said attachment plate to said screw plate leg and to said femur shaft.

7. The femur shaft screw plate of claim 5 and in which said first flange and said second flange are in generally rectangular configuration and said screw holes disposed in each respective flange are offset from said screw holes disposed along said first length of said screw plate leg.

8. A reinforcing plate as in claim 1 wherein said reinforcing plate further includes at least two centrally disposed screw holes, disposed in said raised member and two screw holes of said at least two centrally disposed screw holes aligned with said two screw holes in said screw plate leg, said two screw holes of said at least two centrally disposed screw holes in said raised member for permitting passage of shafts of femur shaft screws through said raised member and through said screw plate leg for securing said reinforcing plate to said femur screw plate and for securing said reinforcing plate and said femur screw plate, as a combined unit to the exterior of said femur shaft.

* * * * *